United States Patent [19]
Patchett et al.

[11] 4,389,237
[45] Jun. 21, 1983

[54] THIOLCARBAMATE SULFOXIDES PROTECTED AGAINST DRY SOIL DEACTIVATION

[75] Inventors: Gilbert G. Patchett, Richmond; Reed A. Gray, Saratoga, both of Calif.; Daniel L. Hyzak, Austin, Tex.

[73] Assignee: Stauffer Chemical Company, Westport, Conn.

[21] Appl. No.: 304,539

[22] Filed: Sep. 23, 1981

[51] Int. Cl.³ .............................................. A01N 41/00
[52] U.S. Cl. ............................................ 71/103; 71/94; 71/95; 71/88; 71/113; 71/114
[58] Field of Search .................. 71/94, 95, 88, 103, 71/113, 114

[56] References Cited

U.S. PATENT DOCUMENTS

| | | | |
|---|---|---|---|
| 3,598,859 | 8/1971 | Yates et al. | 71/100 |
| 3,896,169 | 7/1975 | Tilles et al. | 71/100 |
| 3,928,436 | 12/1975 | Tilles et al. | 71/100 |
| 3,989,684 | 11/1976 | Tilles | 71/103 |
| 4,008,071 | 2/1977 | Gozzo et al. | 71/103 |
| 4,081,468 | 3/1978 | Baker et al. | 71/103 |
| 4,117,010 | 9/1978 | Baker et al. | 71/103 |
| 4,314,841 | 2/1982 | Scher | 71/103 |

*Primary Examiner*—James H. Reamer
*Attorney, Agent, or Firm*—Edwin H. Baker

[57] ABSTRACT

Herbicidal thiolcarbamate sulfoxide compositions of improved stability.

15 Claims, No Drawings

THIOLCARBAMATE SULFOXIDES PROTECTED AGAINST DRY SOIL DEACTIVATION

This invention relates to a process for protecting thiolcarbamate sulfoxide herbicides against dry soil deactivation and to a composition for obtaining this result.

BACKGROUND OF THE INVENTION

Thiolcarbamate sulfoxide herbicides that are the subject of the present invention have been disclosed in U.S. Pat. No. 3,897,492, 3,928,436, 3,598,859, 3,989,684 and various foreign patents.

These compounds exhibit excellent herbicidal activity against a variety of undesirable grasses and broadleaf plants. However, it has been discovered that their herbicidal activity is reduced when they are utilized in dry soil.

In other words, when the sulfoxide herbicide is applied to dry soil or applied to soil that becomes dry after application, deactivation of the herbicide occurs with resulting reduction of herbicidal activity. Generally such deactivation is most troublesome in those soils that contain relatively low amounts of clay, for example, sandy loam soil and those soils that are low in organic matter.

These soils tend to lose moisture more quickly and to a greater degree than soils that contain higher amounts of clay. Conversely, in those soils that contain relatively higher amounts of clay, the deactivation of the sulfoxide herbicide is less troublesome.

The term "dry soil" as used herein means soil that contains less than about 10 percent moisture. When the moisture level in the soil is less than about 10 percent, deactivation of the sulfoxide herbicide has been observed. Moisture levels of less than 6–7 percent cause severe deactivation of the sulfoxide herbicide.

DESCRIPTION OF THIS INVENTION

The herbicidal activity of certain thiolcarbamate sulfoxides can be maintained in dry soil by combining a Lewis acid with these sulfoxide herbicides before application to the soil where herbicidal control is desired.

Accordingly, one embodiment of this invention relates to a novel composition of matter comprising:

(a) about 10 to about 90 percent by weight of a thiolcarbamate sulfoxide of the formula $$R-CH_2-S(O)-C(O)-N(R_1)(R_2)$$

wherein

R is alkyl $C_1-C_7$, preferably $C_1-C_4$; haloalkyl $C_1-C_5$, preferably chloroalkyl $C_1-C_3$; alkoxy $C_1-C_5$, preferably $C_1-C_3$; and phenyl;

$R^1$ and $R^2$ independently are alkyl $C_1-C_6$, preferably $C_2-C_4$; cycloalkyl $C_3-C_8$, preferably cyclohexyl; alkenyl $C_2-C_6$; and alkynyl $C_2C_4$; or $R^1$ and $R^2$ together form an alkylene ring having 4 to 7 carbon atoms optionally substituted with one or two $C_1-C_4$ alkyl groups and preferably $R^1$ and $R^2$ together with the nitrogen atom to which they are attached form piperidino, hexamethyleneimino, decahydroquinolyl, 2,5-dimethylpiperidino and 5-ethyl-2-methylpiperidino; and correspondingly (b) about 90 to about 10 percent by weight of a Lewis acid.

Preferably, the novel composition of matter comprises (a) about 40 to about 60 percent by weight thiolcarbamate sulfoxide and (b) about 60 to about 40 percent by weight of the Lewis acid.

Any Lewis acid is useful as the stabilizer in the practice of this invention. Preferred acids are neohexanoic acid, phosphoric acid, benzoic acid, and lactic acid. These acids are preferred because of their relative efficiency, low cost and safeness.

The herbicidal thiolcarbmate sulfoxides stabilized in accordance with this invention are described in several publications, including, U.S. Pat. Nos. 3,897,492, 3,928,436, 3,879,455 and 3,989,684. Some examples of compounds of this type are: S-ethyl N,N-di-n-propyl carbamyl sulfoxide, S-ethyl N,N-di-i-butyl carbamyl sulfoxide, S-n-butyl N,N-di-isobutyl carbamyl sulfoxide, S-n-butyl N,N-di-isobutyl carbamyl sulfoxide, S-n-propyl N-n-butyl-N-ethyl carbamyl sulfoxide, S-ethyl N-cyclohexyl-N-ethyl carbamyl sulfoxide, S-ethyl N-methyl-N-α-methylpropargyl carbamyl sulfoxide, S-n-propyl N,N-di-n-propyl carbamayl sulfoxide, S-ethyl N-allyl-N-n-propyl carbamyl sulfoxide, S-n-chloropropyl N,N-diethyl carbamyl sulfoxide, S-ethoxyethyl N,N-di-n-propyl carbamyl sulfoxide, S-isobutyl N-methyl-N-cyclohexylmethyl carbamyl sulfoxide, S-ethyl-hexahydro-1H-azepine-1-carbonyl sulfoxide, S-1,2-dichloropropyl N,N-di-i-propyl carbamyl sulfoxide and the like.

The term "alkyl" as used herein refers to straight- or branched-chain saturated aliphatic hydrocarbon groups, i.e., methyl, ethyl, propyl, i-propyl, n-butyl, s-butyl and t-butyl, the amyls, the hexyls and the heptyls.

The term "alkoxy" as used herein refers to a straight- or branched-chain saturated aliphatic hydrocarbonoxy group, i.e., methoxy, ethoxy, propoxy, i-propoxy, n-butoxy, i-butoxy, s-butoxy, and t-butoxy.

The term "halo" as used herein refers to chloro, bromo, and ily done in a tank-mix application of herbicides. The amount of water is not critical and can be any amount that is convenient for a spray application of the sulfoxide herbicide.

The Lewis acid can be used as either a free acid or it can be used as its sodium or potassium salt.

The following examples illustrate the stabilizing effect of various Lewis acids including both organic and inorganic acid additives as dry soil stabilizers for a representative thiolcarbamate sulfoxide.

EXAMPLE I

An aqueous solution containing 0.1 percent (%) by weight S-n-propyl-N,N-diisobutyl thiolcarbamate sulfoxide having the structural formula $$CH_3CH_2CH_2-S(O)-C(O)-N(CH_2-CH(CH_3)-CH_3)_2$$

was prepared.

Similar aqueous solutions containing the same amount of sulfoxide compound and various amounts of several acid stabilizers were also prepared.

Twenty gram (g) samples of sandy loam soil were weighed into 4-ounce wide-mouth bottles. Next 200 microliters (ul) of the solution containing only the sulfoxide compound were added dropwise to the surface of a soil sample. This addition resulted in 10 parts per million (ppm) sulfoxide compound being added to the soil sample.

Similarly, solutions containing sulfoxide compound and an acid additive were added to a soil sample. The amount of acid additive that was added to each soil sample is recited in Table I.

The sealed jars were incubated at 84° F. for 18 hours and then extracted with 20 milliliters (ml) of 50% isopropanol in water by shaking for 60 minutes. The crude extract was centrifuged for 10 minutes at 1500 RPM to obtain a clear extract containing any remaining sulfoxide compound which was quantitatively determined by liquid chromatography.

The liquid chromatography equipment consisted of a Beckman Model 324 pump system, a 15 cm, 5 micron Ultrasphere ODS reverse phase column, and a DuPont U.V. Spectrometer variable wavelength detector. The eluting solvent was 50% v/v acetonitrile in water and the detector was set at 230 nm. Ten microliter aliquots of the sample extracts and reference standards were injected into the liquid chromatograph, the peak heights of the sulfoxide compound were measured, and the ppm of the sulfoxide compound remaining in the soil was calculated. The slope of the degradation curve on semi-log paper was used to determine the half-life value of the sulfoxide compound in the soil. The improvement factor was calculated by dividing the half-life value found for the sulfoxide compound alone into the half-life value found for the sufoxide compound plus acid additive and is reported in Table I.

TABLE I

| Acid Additive | Amount (ppm) | Improvement Factor |
|---|---|---|
| none | — | 1.00 |
| acetic | 20 | 1.52 |
| propionic | 20 | 1.48 |
| butynic | 20 | 1.73 |
| valeric | 20 | 2.19 |
| adipic | 20 | 1.43 |
| acrylic | 20 | 1.29 |
| benzoic | 20 | 1.30 |
| ortho-phthalic | 40 | 1.74 |
| butyric | 80 | 2.66 |
| neohexanoic | 5 | 2.37 |
| neohexanoic | 20 | 2.90 |
| hydrochloric, 37% | 40 | 1.61 |
| sulfuric, 96% | 20 | 1.80 |
| phosphoric, 86% | 20 | 1.90 |
| phosphoric, 86% | 40 | 2.49 |

EXAMPLE 2

The following example shows the effectiveness of various Lewis acids in protecting a representative thiolcarbamate sulfoxide against dry soil deactivation.

The test was conducted by placing 100 milliliters (ml) of air dried, sandy loam soil into a 8.5×6.0×3 inch aluminum flat in a layer ⅛ inch deep. Sufficient S-n-propyl-N,N-di-n-propyl carbamyl sulfoxide dissolved in 3 ml acetone were sprayed onto the surface of the dry soil at a rate of 3 lb/A using a No. 152 DeVilbiss atomizer at an air pressure of 5 pounds per square inch (psi).

Other tests were conducted by combining various Lewis acid additives with the sulfoxide in acetone solutions and applying the combination to the surface of the dry soil. The rate of application of the acid additive was 3 lb/A and the rate of application of the sulfoxide was 3 lb/A.

After spraying, the flats were placed in a greenhouse at 70°-85° F. for three days and kept dry. Then the treated soil was mixed with moist sandy loam soil and returned to the aluminum flat. Sufficient moist soil was used to fill the flat to maximum depth. Next seeds of three grasses—watergrass (*Echinochloa crusgalli*), green foxtail (*Setaria viridis*), and wild oats (*Avena fatua*), were planted in rows. Ample seeds were planted to give about 20 to 50 seedlings per row after emergence.

As a control, sufficient S-n-propyl-N,N-di-n-propyl carbamyl sulfoxide dissolved in 3 ml acetone was sprayed onto the surface of the air dried soil sample at a rate of 3 lb/A using the atomizer. The sprayed compound was immediately mixed with the moist soil and returned to the flat. This flat was placed in the greenhouse and stored for three days before the planting of the three grasses as described above.

After seed planting, all flats were returned to the greenhouse for three weeks growing at 70° to 85° F. and were watered daily by sprinkling. After three weeks, the degree of injury or control was determined by comparison with untreated check plants of the same age.

The injury rating from 0 to 100% was recorded for each grass species as percent control with 0% representing no control and 100% representing complete control and are reported in Table II.

TABLE II

Effect of various Lewis acid additives on S—n-propyl—N,N—di-n-propyl carbamyl sulfoxide in dry soil

| Acid Additive[1] | Additive Amount lb/A | Average Percent Weed Control on 3 Grasses 3 Weeks After Treatment |
|---|---|---|
| none (sulfoxide alone at 3 lb/A) | 0 | 36 |
| succinic | 3 | 82 |
| galacturonic | 3 | 82 |
| lactic | 3 | 84 |
| pyruvic | 3 | 87 |
| palmitic | 3 | 80 |
| stearic | 3 | 57 |
| oleic | 3 | 65 |
| phenylacetic | 3 | 62 |
| tartaric | 3 | 48 |
| octanoic | 3 | 73 |
| decanoic | 3 | 72 |
| lauric | 3 | 78 |
| hexanoic | 3 | 57 |
| l-naphthoic | 3 | 70 |
| glycolic | 3 | 60 |
| fumaric | 3 | 62 |
| oxalic | 3 | 53 |
| trichloroacetic | 3 | 78 |
| propionic | 3 | 50 |
| picric | 3 | 20 |
| humic | 3 | 50 |
| neohexanoic | 3 | 62 |
| neodecanoic | 3 | 40 |
| phosphoric | 3 | 67 |
| none (sulfoxide alone at 3 lb/A)[2] | 0 | 97 |

[1]The acid additives have been found to have no herbicidal activity at 3 lb/A.
[2]S—n-propyl—N,N—di-n-propyl carbamyl sulfoxide was applied at 3 lb/A on the surface of the dry soil and was immediately mixed with the moist soil. No acid additive was used.

The results in Table II show that when the sulfoxide compound without an acid additive is applied as a thin layer on the surface of dry soil and not incorporated into the moist soil until 3 days after treatment, then most of the herbicidal activity is lost. The results show that all acid additives protect the sulfoxide against dry soil deactivation.

The following example illustrates the stabilizing effect of various salts of Lewis acids as dry soil stabilizers for a representative thiolcarbamate sulfoxide.

EXAMPLE 3

This test was conducted the same as Example II except that salts of Lewis acids were used as the acid additive and they were dissolved in a 3 ml solution of 50:50 acetone-water.

The results are reported in Table III.

TABLE III

Effect of various Lewis acid salt additives on S—n-propyl—N,N—di-n-propyl carbamyl sulfoxide in dry soil

| Acid Salt Additive[1] | Additive Amount lb/A | Average Percent Weed Control on 3 Grasses 3 Weeks After Treatment |
|---|---|---|
| none (sulfoxide alone at 3 lb/A) | 0 | 67 |
| sodium lactate | 3 | 72 |
| sodium laurate | 3 | 94 |
| sodium palmatate | 3 | 72 |
| sodium pyruvate | 3 | 83 |
| none (sulfoxide alone at 3 lb/A)[2] | 0 | 98 |

[1]The acid salt additives have been found to have no herbicidal activity at 3 lb/A.
[2]S—n-propyl—N,N—di-n-propyl carbamyl sulfoxide was applied at 3 lb/A on the surface of the dry soil and was immediately mixed with the moist soil. No acid additive was used.

In general, any conventional method of application can be used. The locus of application is the soil. Soil application can be achieved by conventional ground or air application equipment. The compositions are applied to the soil surface and optionally incorporated.

The amount of the present composition which constitutes a herbicidally effective amount depends upon the nature of the plants to be controlled. The rate of application of active ingredients varies from about 0.01 to about 50 pounds per acre, preferably about 0.1 to about 25 pounds per acre with the actual amount used depending on the overall cost and the desired results.

The compositions of the present invention can be directly used as a herbicide without formulation with other ingredients. Preferably, the composition is diluted with water and applied as a herbicide in that form.

A surfactant can be included with the composition if desired. Such agents will usually comprise up to about 5 weight percent of the total composition.

The compositions of the present invention are useful in controlling the growth of undesirable vegetation by pre-emergence or post-emergence application to the locus where control is desired, including pre-plant and post-plant soil incorporation as well as surface application.

What is claimed is:
1. A herbicidal composition comprising combining
(a) about 10 to about 90 percent by weight of a thiolcarbamate sulfoxide of the formula

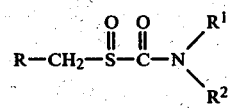

in which
R is alkyl $C_1$-$C_7$, haloalkyl $C_1$-$C_5$, alkoxy $C_1$-$C_5$ and phenyl;
$R^1$ and $R^2$ independently are alkyl $C_1$-$C_6$, cycloalkyl $C_3$-$C_8$, alkenyl $C_2$-$C_6$ and alkynyl $C_2$-$C_4$; or
$R^1$ and $R^2$ together form an alkylene ring having 4 to 7 carbon atoms optionally substituted with one or two $C_1$-$C_4$ alkyl groups and preferably $R^1$ and $R^2$ together with the nitrogen atom to which they are attached form piperidino, hexamethyleneimino, decahydroquinolyl, 2,5-dimethylpiperidino and 5-ethyl-2-methylpiperidino; and
(b) about 90 to about 10 percent by weight of neohexanoic acid, phosphoric acid, benzoic acid, lactic acid or their sodium or potassium salts.

2. The composition according to claim 1 wherein the thiolcarbamate sulfoxide is present in an amount between about 40 percent by weight to about 60 percent by weight and the acid or its salt is present in an amount between about 60 percent by weight to about 40 percent by weight.

3. The composition according to claim 1 wherein the thiolcarbamate sulfoxide is S-n-propyl N,N-di-n-propyl carbamyl sulfoxide.

4. The composition according to claim 2 wherein the thiolcarbamate sulfoxide is S-n-propyl N,N-di-n-propyl carbamyl sulfoxide.

5. The composition according to claim 1 wherein R is alkyl $C_1$-$C_7$, $R^1$ and $R^2$ independently are alkyl $C_1$-$C_6$, cycloalkyl $C_3$-$C_8$ or $R^1$ and $R^2$ taken together with the nitrogen atom to which they are attached form piperidino, hexamethyleneimino, decahydroquinolyl, 2,5-dimethylpiperidino and 5-ethyl-2-methylpiperidino.

6. The composition according to claim 1 wherein R is alkyl $C_2$-$C_4$, $R^1$ and $R^2$ independently are alkyl $C_1$-$C_6$.

7. A method of controlling undesirable vegetation which comprises applying to the area where control is desired an herbicidally effective amount of a herbicidal composition comprising combining
(a) about 10 to about 90 percent by weight of a thiolcarbamate sulfoxide of the formula

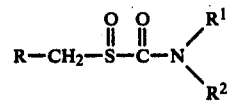

in which
R is alkyl $C_1$-$C_7$, haloalkyl $C_1$-$C_5$, alkoxy $C_1$-$C_5$ and phenyl;
$R^1$ and $R^2$ independently are alkyl $C_1$-$C_6$, cycloalkyl $C_3$-$C_8$, alkenyl $C_2$-$C_6$ and alkynyl $C_2$-$C_4$; or
$R^1$ and $R^2$ together form an alkylene ring having 4 to 7 carbon atoms optionally substituted with one or two $C_1$-$C_4$ alkyl groups and preferably $R^1$ and $R^2$ together with the nitrogen atom to which they are attached form piperidino, hexamethyleneimino, decahydroquinolyl, 2,5-dimethylpiperidino and 5-ethyl-2-methylpiperidino; and (b) about 90 to about 10 percent by weight of neohexanoic acid, phosphoric acid, benzoic acid, lactic acid of their sodium or potassium salts.

8. The method according to claim 7 wherein the thiolcarbamate sulfoxide is present in an amount between about 40 percent by weight to about 60 percent by weight and the acid or its salt is present in an amount between about 60 percent by weight to about 40 percent by weight.

9. The method according to claim 7 wherein the thiolcarbamate sulfoxide is S-n-propyl N,N-di-n-propyl carbamyl sulfoxide.

10. The method according to claim 8 wherein the thiolcarbamate sulfoxide is S-n-propyl N,N-di-n-propyl carbamyl sulfoxide.

11. The method according to claim 7 wherein R is alkyl $C_1$–$C_7$, $R^1$ and $R^2$ independently are alkyl $C_1$–$C_6$, cycloalkyl $C_3$–$C_8$ or $R^1$ and $R^2$ taken together with the nitrogen atom to which they are attached form piperidino, hexamethyleneimino, decahydroquinolyl, 2,5-dimethylpiperidino and 5-ethyl-2-methylpiperidino.

12. The method according to claim 7 wherein R is alkyl $C_2$–$C_4$, $R^1$ and $R^2$ independently are alkyl $C_1$–$C_6$.

13. An aqueous mixture of the herbicidal composition of claim 1.

14. An aqueous mixture of the herbicidal composition of claim 5.

15. An aqueous mixture of the herbicidal composition of claim 3.

* * * * *